United States Patent [19]
Minick et al.

[11] Patent Number: 5,462,256
[45] Date of Patent: Oct. 31, 1995

[54] PUSH BUTTON FLOW STOP USEABLE WITH A DISPOSABLE INFUSION PUMPING CHAMBER CASSETTE

[75] Inventors: Steven E. Minick, San Diego; Michael W. Lawless, Poway; Peter A. Soberon, Cardiff; Ashok Kaul, San Diego; Robert A. Hermann, Chula Vista, all of Calif.

[73] Assignee: Abbott Laboratories, Abbott Park, Ill.

[21] Appl. No.: 242,761

[22] Filed: May 13, 1994

[51] Int. Cl.⁶ ..................................... F04B 49/10
[52] U.S. Cl. ................ 251/331; 417/479; 604/153
[58] Field of Search ............. 251/9, 331; 417/479; 604/153

[56] References Cited

U.S. PATENT DOCUMENTS

| | | |
|---|---|---|
| 1,651,964 | 12/1927 | Nelson . |
| 1,764,712 | 6/1930 | Brackett et al. . |
| 2,667,184 | 1/1954 | Hailer . |
| 2,980,032 | 4/1961 | Schneider . |
| 2,988,001 | 6/1961 | D'Arcey et al. . |
| 3,124,214 | 3/1964 | Aselman . |
| 3,127,846 | 4/1964 | Kerns . |
| 3,234,943 | 2/1966 | Metz . |
| 3,307,481 | 3/1967 | De Castelet . |
| 3,461,808 | 8/1969 | Nelson et al. . |
| 3,496,872 | 2/1970 | Riester et al. . |
| 3,561,648 | 2/1971 | Humphrey . |
| 3,664,770 | 5/1972 | Palmer . |
| 3,901,231 | 8/1975 | Olson . |
| 3,976,402 | 8/1976 | Lundquist . |
| 3,985,133 | 10/1976 | Jenkins et al. . |
| 4,047,844 | 9/1977 | Robinson ............... 251/9 X |
| 4,411,603 | 10/1983 | Kell . |
| 4,468,222 | 8/1984 | Lundquist . |
| 4,639,245 | 1/1987 | Pastrone et al. . |
| 4,667,924 | 5/1987 | Speidel ............... 251/9 X |
| 4,818,186 | 4/1989 | Pastrone ............... 251/9 X |
| 4,842,584 | 6/1989 | Pastrone . |
| 4,846,636 | 7/1989 | Danby et al. . |
| 4,944,485 | 7/1990 | Daoud ............... 251/9 X |
| 5,085,562 | 2/1992 | Lintel . |
| 5,171,132 | 12/1992 | Miyazaki et al. . |

FOREIGN PATENT DOCUMENTS

| | | |
|---|---|---|
| 528191 | 5/1954 | Belgium . |
| 577326 | 2/1954 | Canada . |
| 800805 | 12/1950 | Germany . |
| 1237836 | 9/1972 | United Kingdom . |

*Primary Examiner*—Robert G. Nilson
*Attorney, Agent, or Firm*—Harry G. Thibault; Thomas M. Breininger

[57] ABSTRACT

A push button flow stop is mounted on a disposable infusion pumping cassette provided for use with a drug infusion pump. The flow stop is operative to enable or to block fluid flow through the cassette in a first mode and to monitor fluid pressure in the cassette in a second mode.

5 Claims, 10 Drawing Sheets

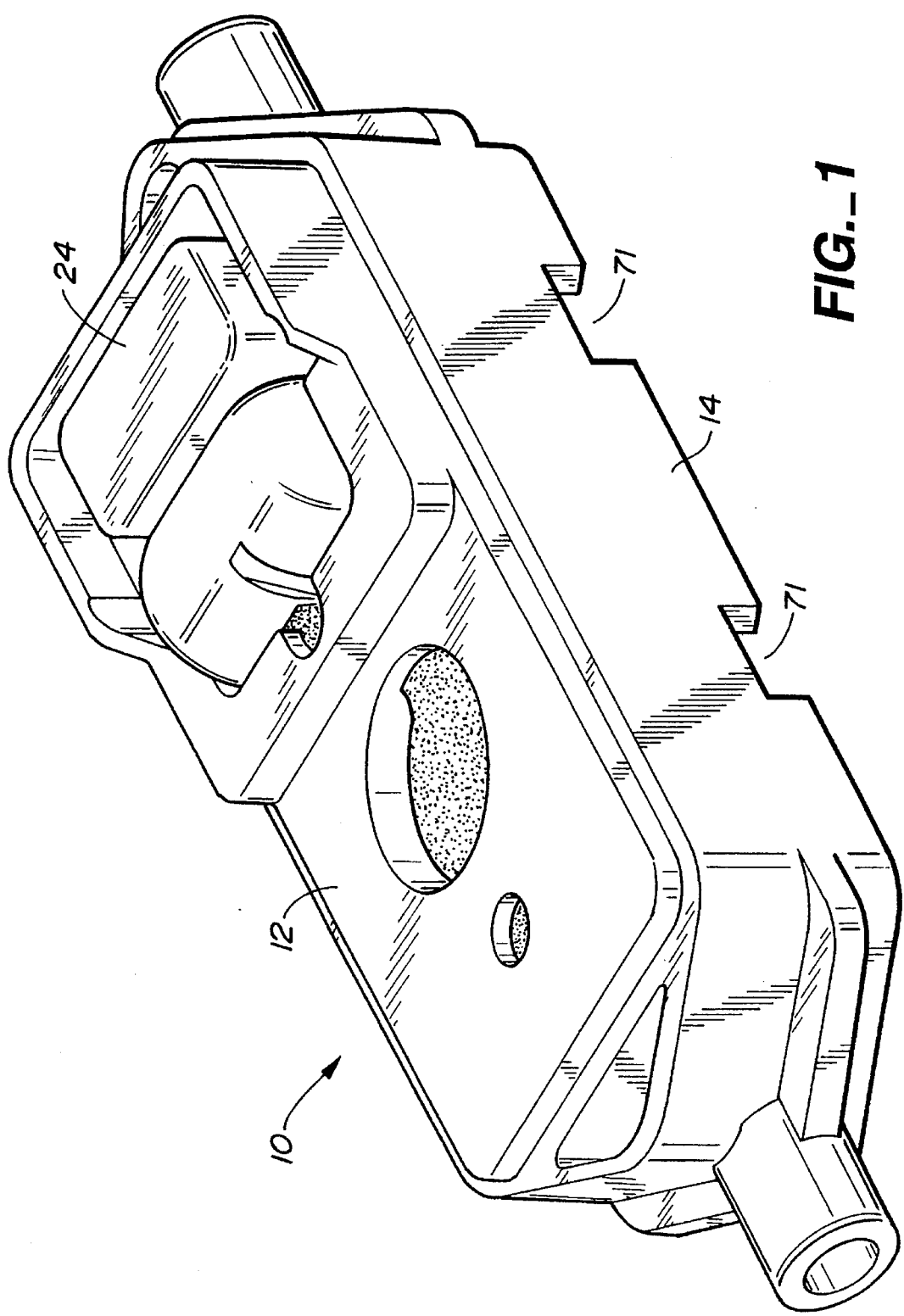
FIG._1

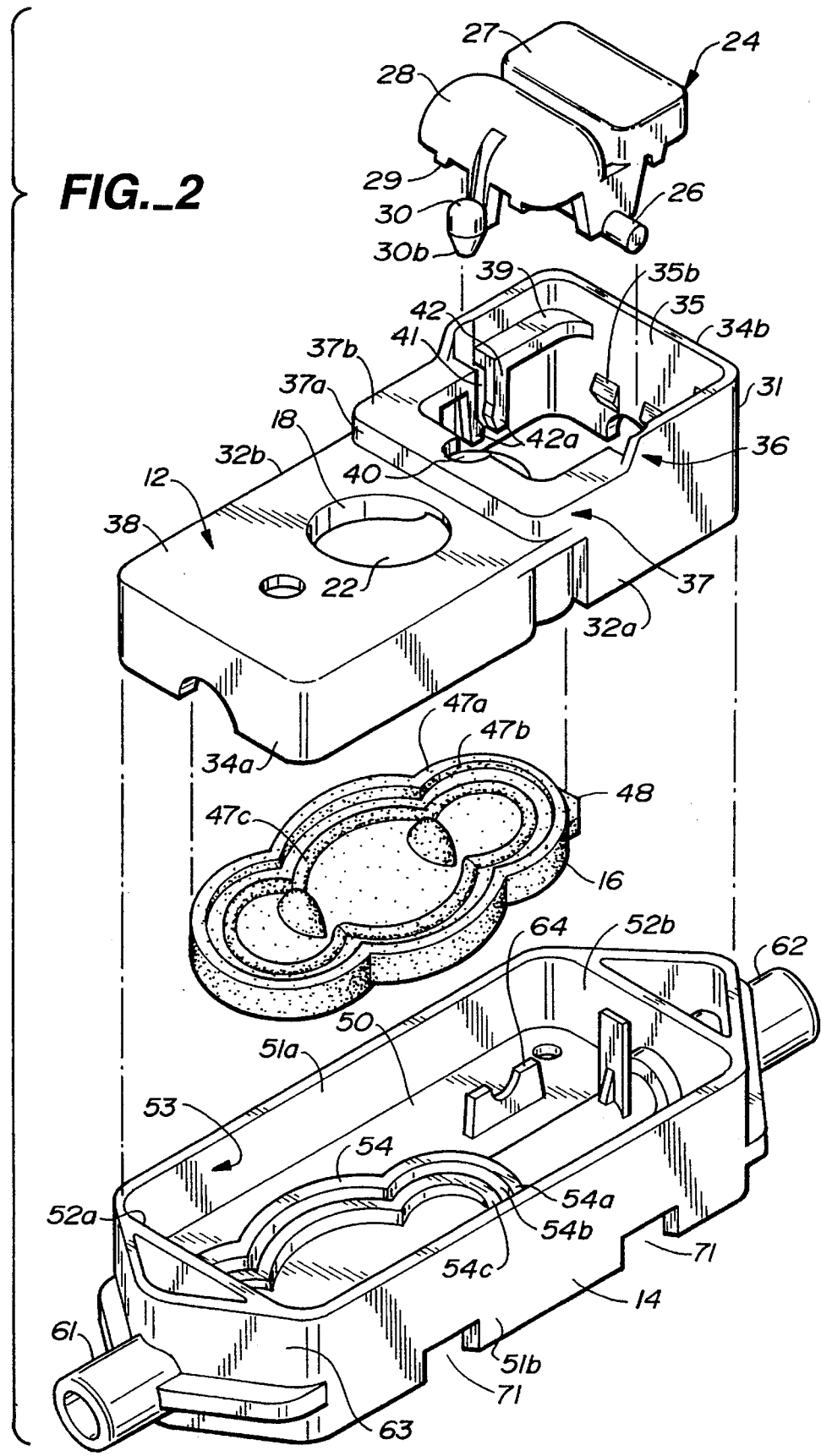
FIG._2

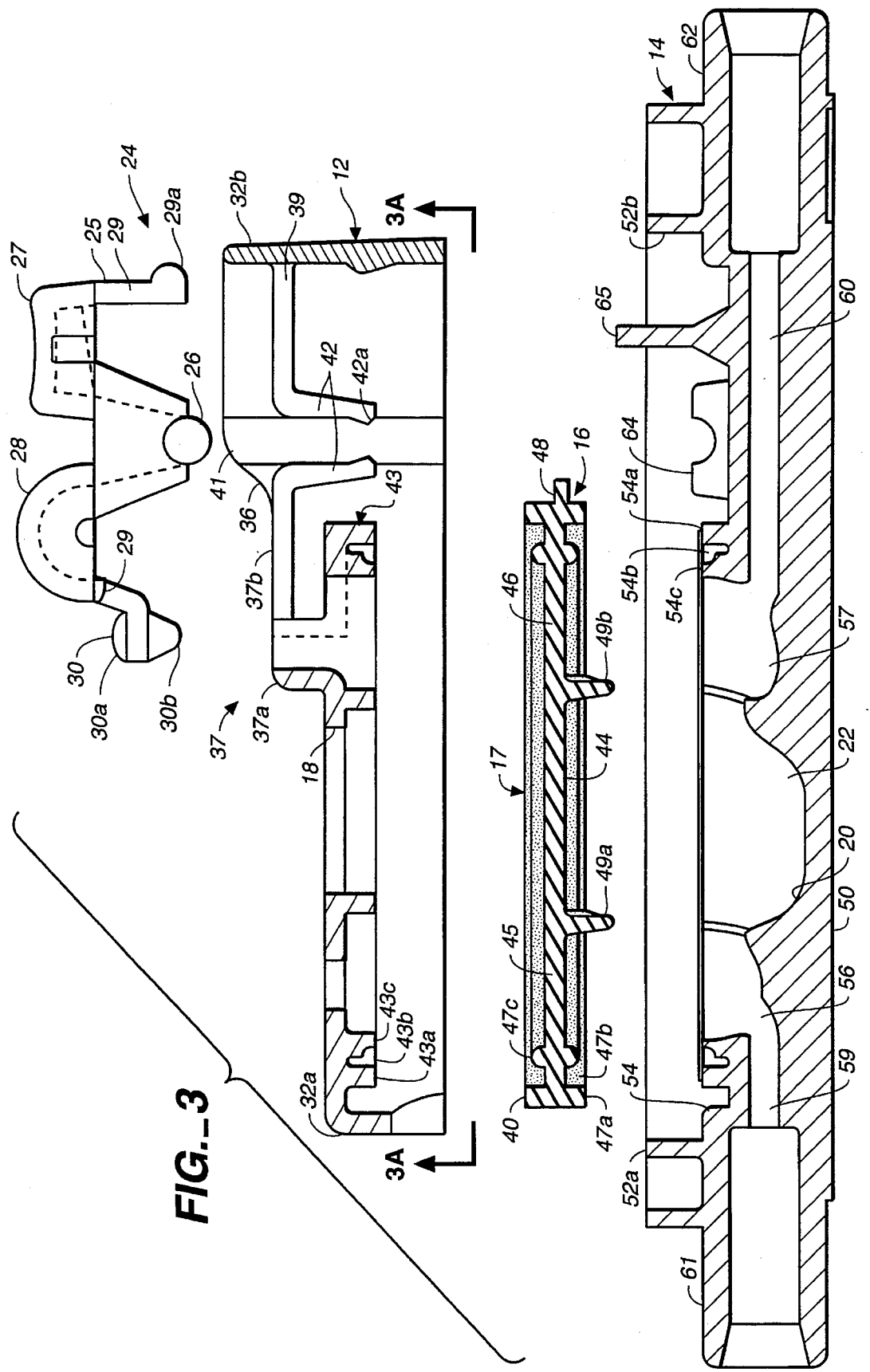

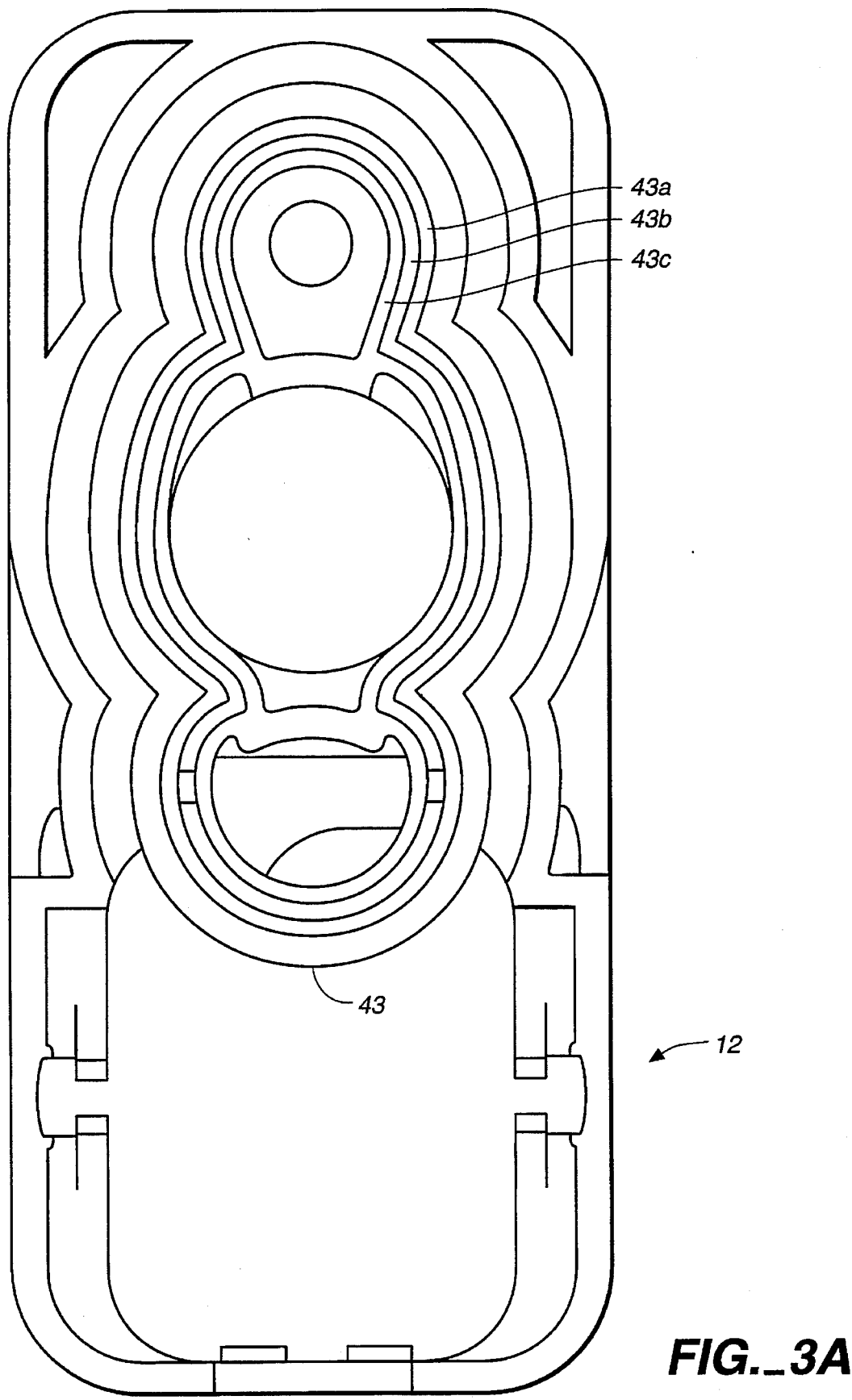
FIG._3A

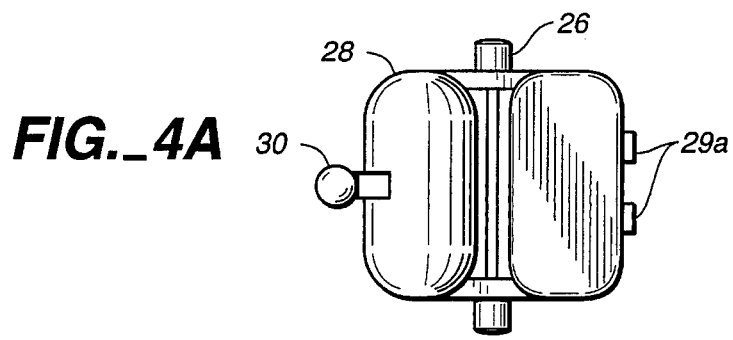
FIG._4A
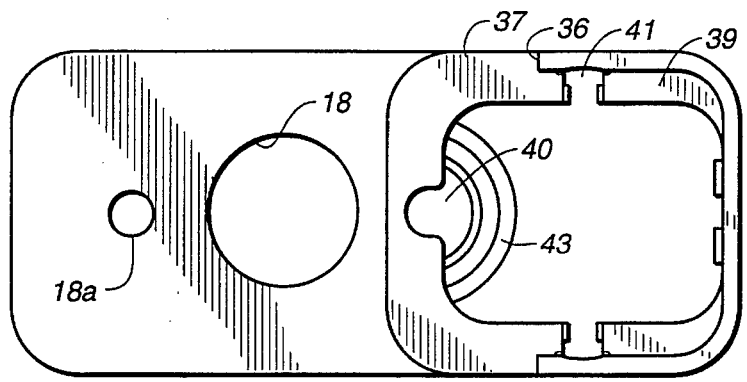
FIG._4B
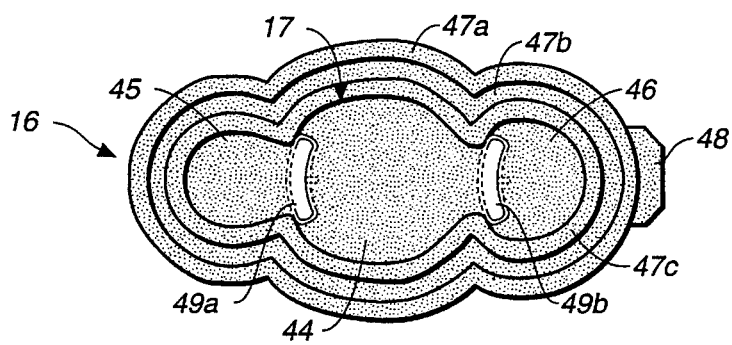
FIG._4C
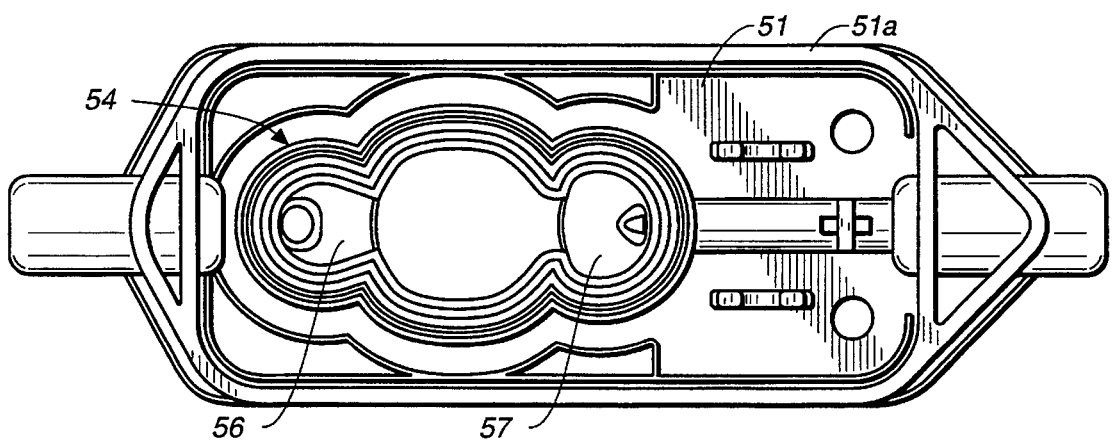
FIG._4D

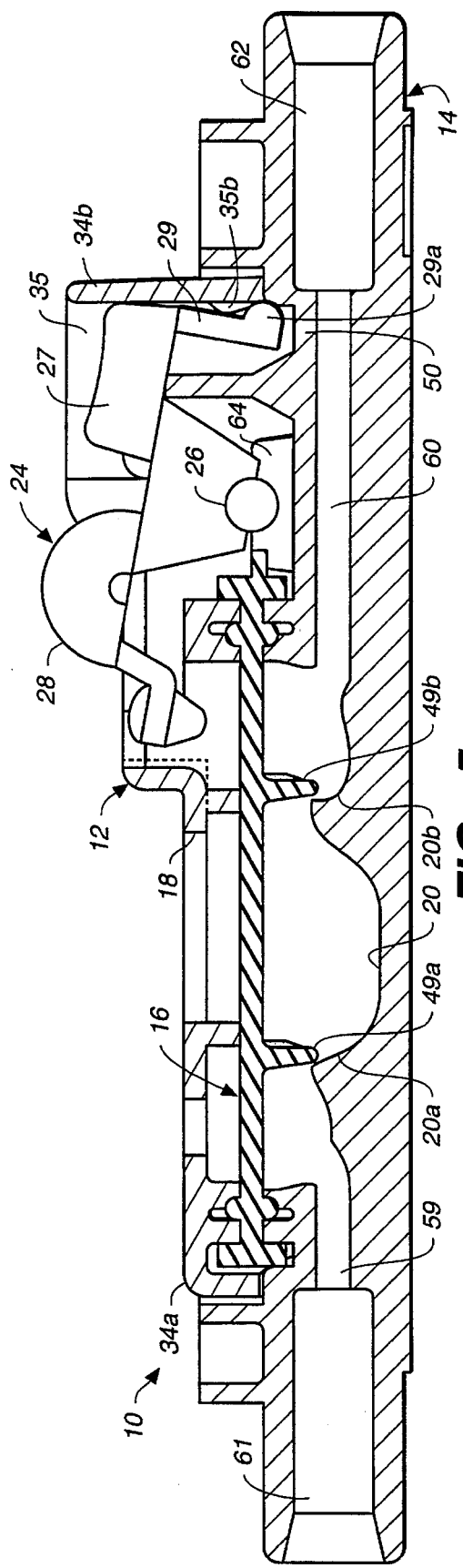

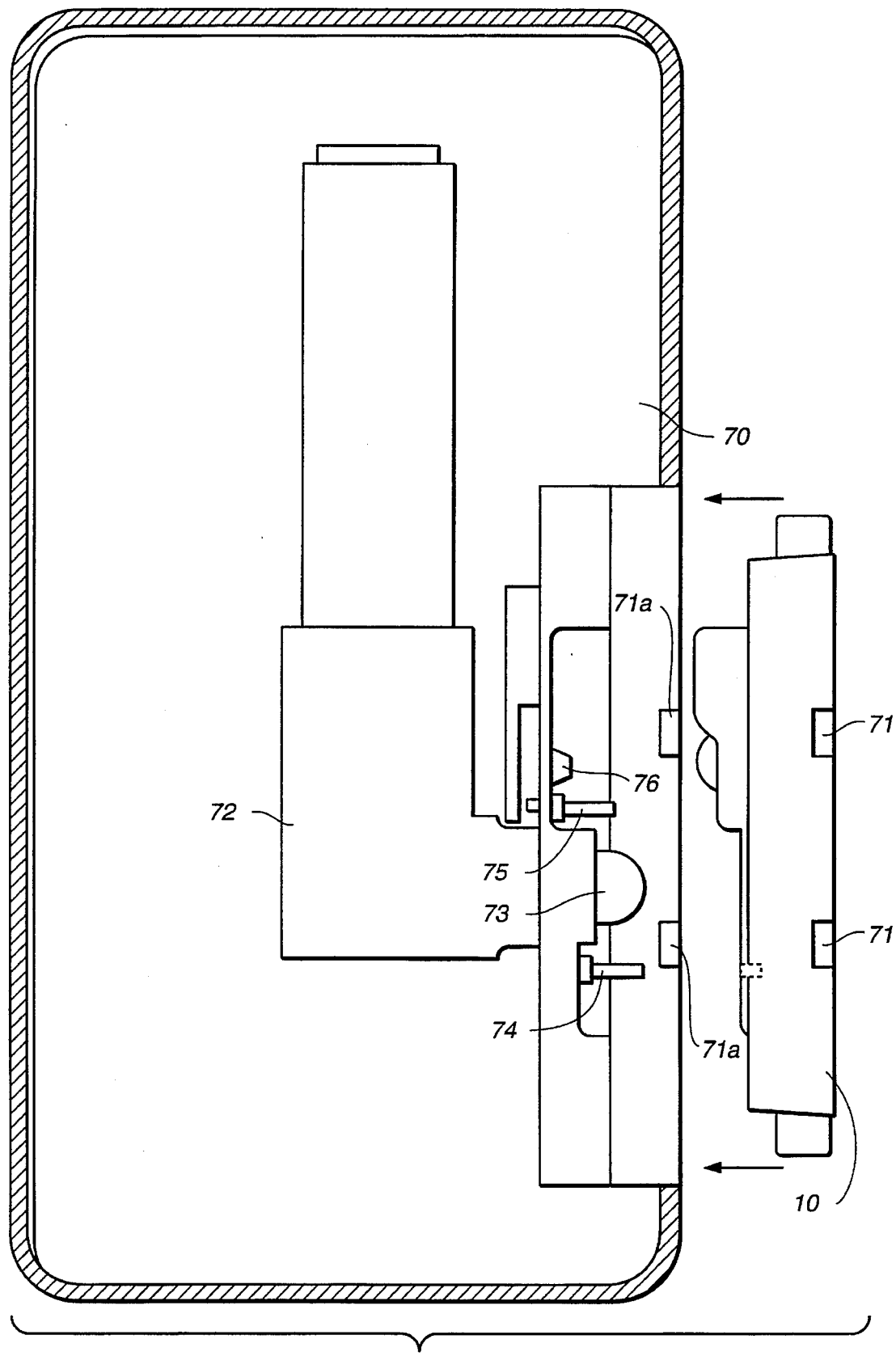
FIG._7

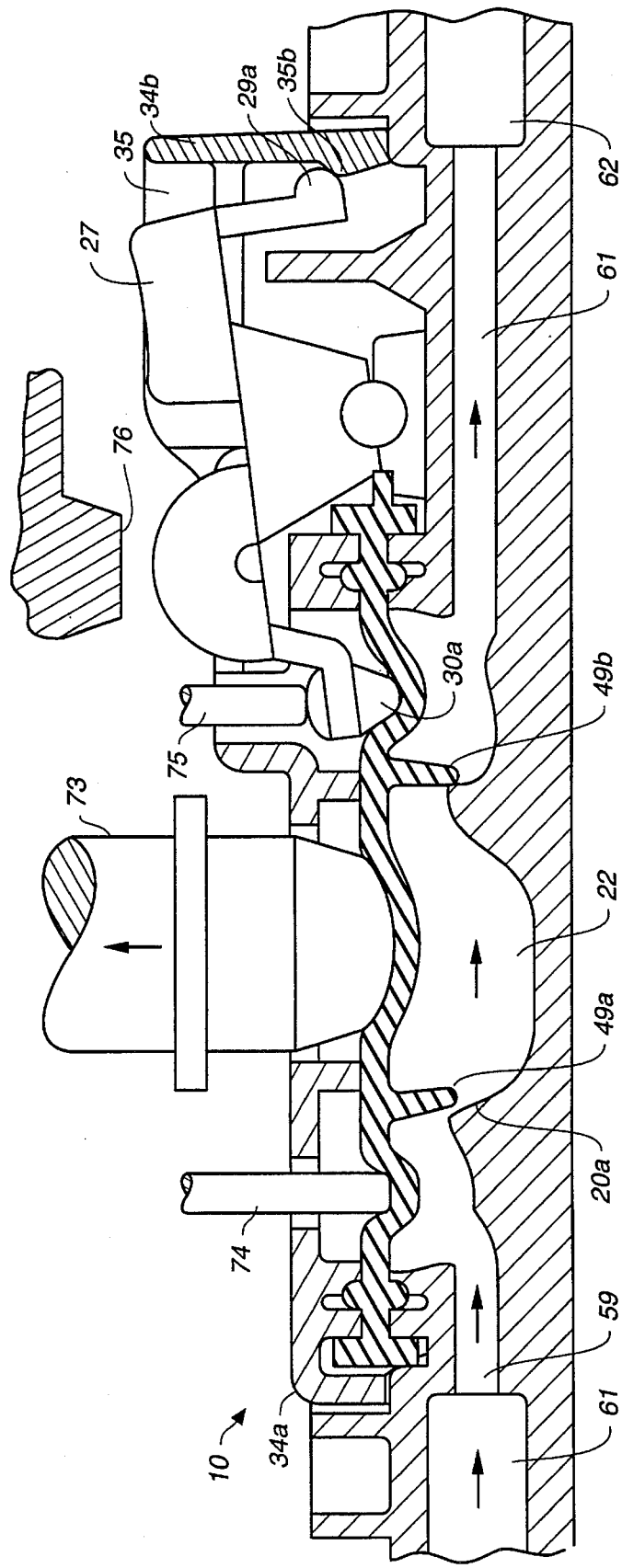
FIG._8

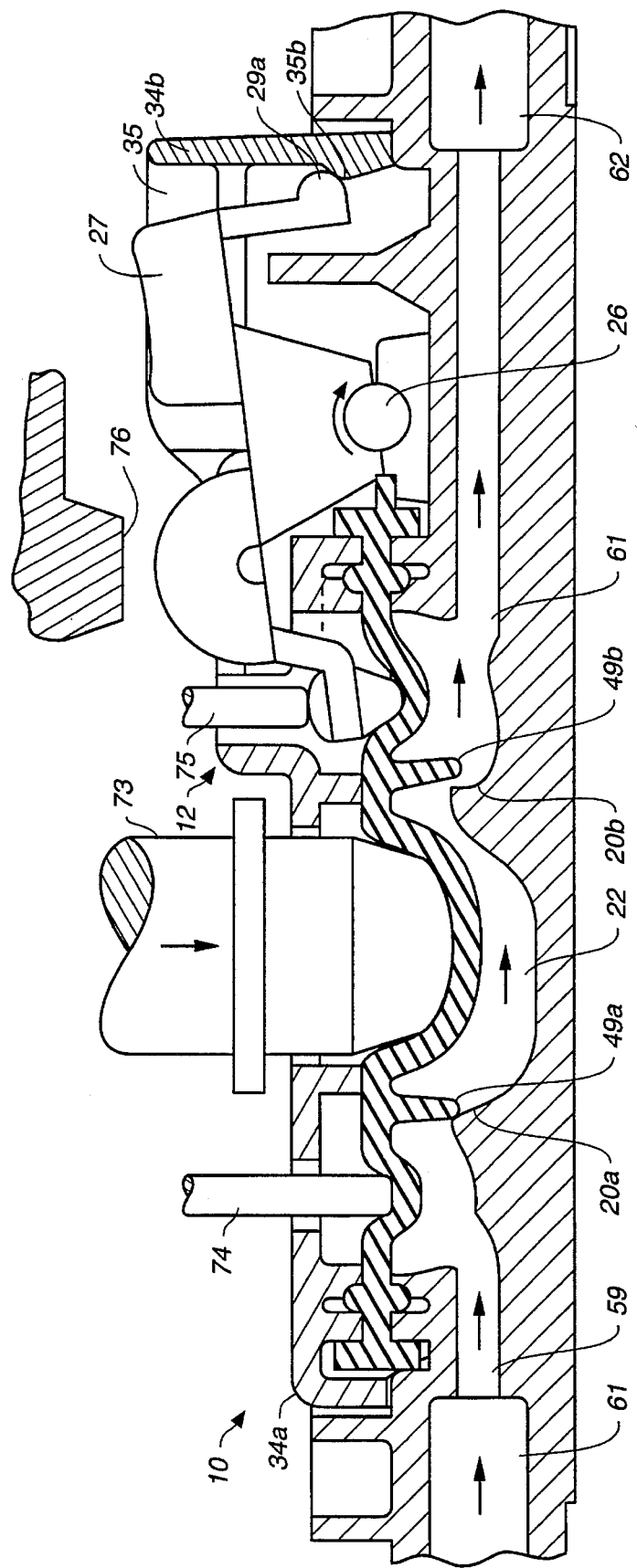
FIG._9

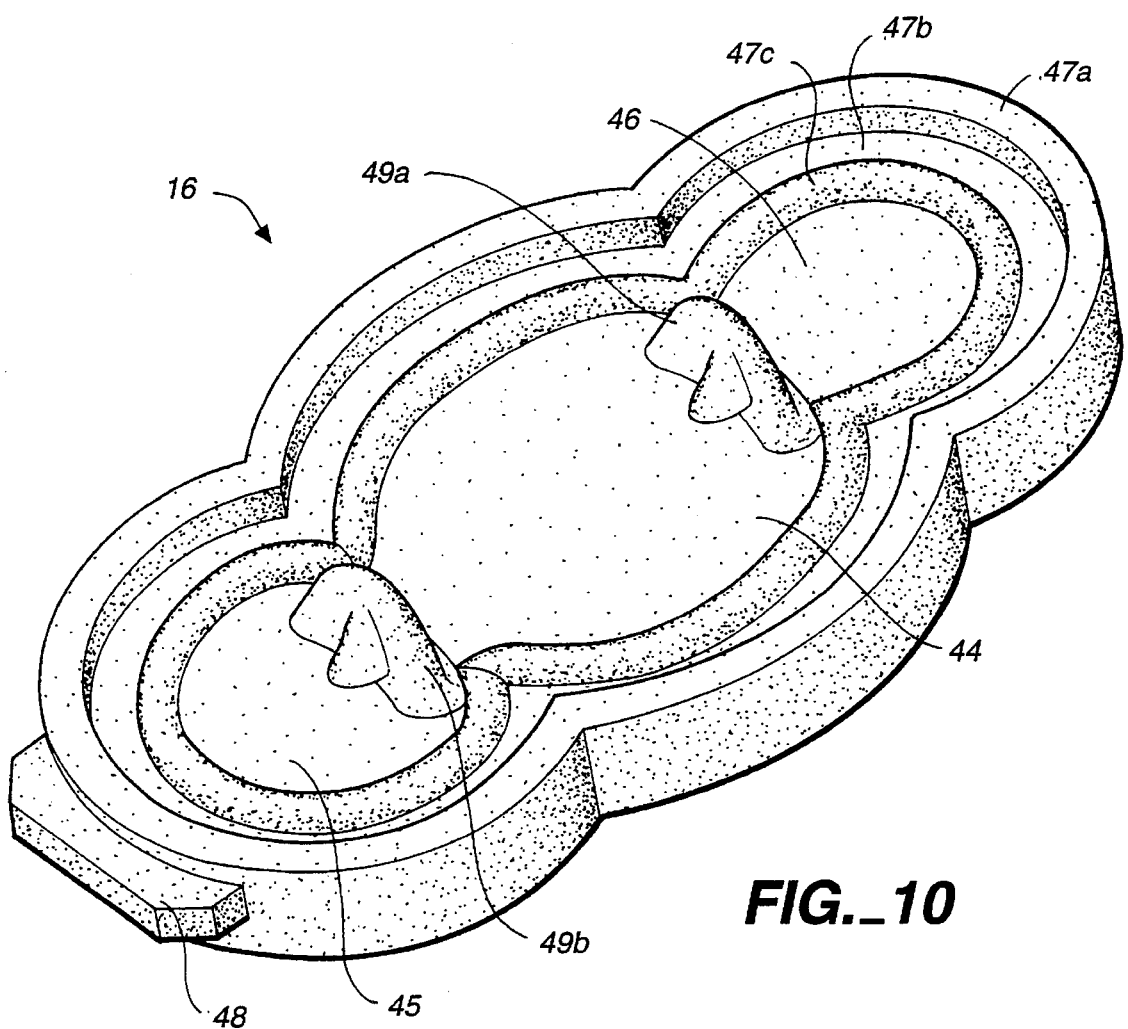
FIG._10

5,462,256

PUSH BUTTON FLOW STOP USEABLE WITH A DISPOSABLE INFUSION PUMPING CHAMBER CASSETTE

RELATED APPLICATIONS

U.S. patent application Ser. No. 08/242,762 entitled "DISPOSABLE FLUID INFUSION PUMPING CHAMBER CASSETTE HAVING A PUSH BUTTON FLOW STOP THEREON" is filed concurrently herewith.

In recent years there has been an increasing use of positive displacement fluid infusion pumping devices for the delivery of fluids intravenously or intra-arterially to a patient. Most frequently such devices are used in hospitals or other patient care locations. Such devices have, to a large extent, replaced the time honored gravity flow control systems, primarily due to their much greater accuracy in delivery rates and dosages, the relative sophistication in permitting a flexible and controlled feed from multiple liquid sources, and in particular their ability to control with precision the amount of potent drugs delivered to a patient over a given period of time.

A typical positive displacement infusion pump system includes a pump driver device and a disposable cassette. The disposable cassette, which is adapted to be used only for a single patient and for one fluid delivery cycle, is typically a small plastic unit having an inlet and an outlet respectively connected through flexible tubing to the fluid supply container and to the patient receiving the infusion. The cassette includes a pumping chamber, with the flow of fluid through the chamber being controlled by a plunger or piston activated in a controlled manner by the driver device.

For example, the cassette chamber may have one wall there formed by a flexible diaphragm which is reciprocated by the plunger and the driver to cause fluid to flow. The pump driver device includes the plunger or piston for controlling the flow of fluid into and out of the pumping chamber in the cassette, and it also includes control mechanisms to assure that the fluid is delivered to the patient at a pre-set rate, in a pre-determined manner, and only for a particular pre-selected time or total dosage. The pump driver device may also include pressure sensing and other fluid flow monitoring devices, as well as valving members for opening and closing various passages in the cassette including the inlet and outlet passages of the pumping chamber.

A disposable pumping chamber cassette of the prior art can be readily and inexpensively manufactured in three pieces. The size of the prior art cassette enables the incorporation of a multiplicity of control and monitoring functions. The prior art cassette includes, for example, pressure monitoring, air bubble detection monitoring, adaptation to multiple inputs, and leak detection monitoring, all of which functions could be performed without modifying the basic cassette structure.

However, putting all of the above described control and monitoring functions on the cassette complicates the prior art cassette with respect to ease of manufacture, functional use and size. In an infusion pumping system which is not dedicated for use in the hospital, but rather is intended for use in the home by the patient or is intended to be carried by the patient in an ambulatory infusion setting, it is desirable to simplify the cassette not only in size, but also in function and in a manner of operation so that the ordinary user can easily use the cassette in the pump on a daily basis, in repeated circumstances, and achieve daily or more frequent installation and use without incident. Moreover, there are increasing ambulatory applications in the hospital which require the simplicity and ease of operation of a cassette designed for home care use.

Although the disposable fluid infusion pumping chamber cassette of the present invention has its genesis in the cassette of the prior art, the present cassette is simpler in structure and in operation and presents a substantially smaller cassette profile, places such control and monitoring functions as air bubble detection monitoring and leak detection monitoring off the cassette to further simplify and shrink the size of the cassette, and provides a pushbutton flow stop to further control fluid delivery through the improved cassette of the present invention.

The cassette of the present invention includes a rigid face member and a rigid back member having an elastomeric diaphragm positioned therebetween. The back member is configured to provide for the transmission of fluid from one end of the cassette to the other and includes an enlarged recess portion forming the pumping chamber. The face member includes an exposed opening opposite the pumping chamber to permit the passage of a plunger. Flow control members, such as check valves, or flapper valves are integrally molded into the elastomeric member and disposed in the fluid path between the inlet and outlet of the cassette to control fluid flow through the cassette.

The so-called flapper valves are disposed on opposite sides of the plunger and placed in the fluid path through the cassette. The cassette includes a cradle support structure for mounting a flow stop on the cassette. The flow stop is a rotatable push button member which is rockable on the cradle support structure between an open position which permits fluid flow through the cassette and an engaged position in which the flow stop stops fluid flow through the cassette.

A better understanding of the present invention can be obtained by a consideration of the detailed description of the invention, particularly when such description is considered in conjunction with the following drawings.

DETAILED DESCRIPTION OF THE DRAWINGS

FIG. 1 is a perspective view of the improved pumping chamber cassette of the present invention;

FIG. 2 is an exploded perspective view of the cassette of FIG. 1;

FIG. 3 is an exploded elevational view of the cassette of FIG. 1;

FIG. 3A is a view taken along lines 3A—3A of FIG. 3;

FIG. 4A is a top plan view of the flow stop of the improved cassette of the present invention;

FIG. 4B is a top plan view of the cover of the improved cassette of the present invention;

FIG. 4C is a top plan view of the elastomeric diaphragm of the improved cassette of the present invention;

FIG. 4D is a top plan view of the base member of the improved cassette of the present invention;

FIG. 5 is an elevational view of the improved cassette of the present invention with the flow stop of the cassette disposed in an open position;

FIG. 6 is an elevational view similar to the view of FIG. 5 wherein the flow stop is in an engaged position;

FIG. 7 is a schematic drawing of a pump and pump driver with the improved cassette of the present invention disposed adjacent thereto for insertion into the pump;

FIG. 8 is an elevational view of the improved cassette of the present invention with the plunger of the pump driver engaging the diaphragm of the cassette in a fluid fill cycle;

FIG. 9 is an elevational view of the improved cassette of the present invention with the plunger of the pump driver engaging the diaphragm of the cassette in a fluid discharge cycle; and FIG. 10 is a top perspective view of the elastomeric diaphragm of the improved cassette of the present invention.

DETAILED DESCRIPTION OF THE PREFERRED EMBODIMENT

A pumping cassette 10 of the present invention is illustrated in FIGS. 1–5. The cassette 10 includes a rigid face member 12 and a rigid back member 14 with an elastomeric member 16 positioned between. Face member 12 has a plunger opening 18 with the elastomeric member 16 extending across the opening. Behind plunger opening 18, in the back member 14, is an enlarged recess 20, which forms the lower fluid reservoir of a pumping chamber 22.

A flow stop 24 comprising a rockable switch body 25 is mounted on the face member 12. Switch body 25 is mounted on a shaft 26 which protrudes from opposite sides of the switch body 24 and further includes at an upper face thereof a concave switch actuator 27 and a convex switch actuator 28.

A leg 29 extends below the concave switch actuator 27. Disposed at a lower end of leg 29 of concave switch actuator 27 is a stop 29a. Disposed at a lower outer end of the convex switch actuator 28 a midpoint thereof is a crown member 30 having an upper end 30a and a lower end 30b.

Face member 12 is a generally rectangularly shaped body 31 having opposite side walls 32a, 32b and end walls 34a and 34b. Each juncture of a side wall 32a, 32b with a respective end wall 34a, 34b is rounded, as best seen in the plan view of FIG. 4B. Face member 12 is about 4.3 centimeters ("cm") long and 1.8 cm wide. An open section 35, at the distal end of the face member 12, is almost square, being slightly longer, at about 2.1 cm, than its width. Distal end wall 34b, adjacent the open section 35 is about 1.1 cm high, about twice the height of proximal end wall 34a (0.55 cm). Side walls 32a, 32b are as high as distal end wall 34b at the juncture therebetween, but step down to the level of proximal end wall 34a in two steps 36 and 37. The first step 36 is at about the mid-point of the open section 35, and the second step 37 is at an inner end 35a of the open section. Upper face 38 which is at the height of proximal end wall 34a, is essentially closed from the riser 37a of the second step 37 to the proximal end wall.

The open section 35 includes opposite interior flanges 39 which extend from the upper face 37b of second step 37 at opposite ends thereof along side walls 32a, 32b to terminate at distal end wall 34b at the inner side thereof. Upper face 37b also includes a semi-circular cutout 40 at a mid-portion thereof, the cutout 40 generally centered along the longitudinal axis of face member 12, with an open face of the cut out 40 opening into section 35.

Provided in opposite interior flanges 39 generally at respective mid-portions thereof are openings 41 further defined by downwardly extending sets of rails or guides 42 provided at opposite peripheral edges of each opening 39 and integrally molded into side walls 32a, 32b. Each rail or guide of each set of rails or guides 42 terminates at a lower end in a detent 42a.

The upper face 38 of face member 12 extends from the bottom of second step 37 to proximal end wall 32a to close upper face 38 except for a plunger opening 18 and a proximal sensor opening 18a disposed between the opening 18 and end wall 32a.

Underlying upper face 38 is an integral face elliptic member 43 centrally disposed about the plunger opening 18 and extending outwardly therefrom toward-opposite end walls 32a, 32b to encompass the first sensor opening 18a and a second sensor opening partially defined by the cut out 40 provided at the inner end of the upper face 37b of second step 37. An outer peripheral ridge 43a of elliptic member 43 and a second peripheral ridge 43c inset therefrom define a peripheral channel 43b therebetween. As shown in FIG. 3, a portion of face elliptic member 43 opposite the cut out opening 40 in face 37b of second step 37 is spaced from the face of step 37.

Elastomeric member 16 is a molded flexible elastomeric member also somewhat elliptic in configuration, which conforms generally to the shape of the face elliptic member 43 at the underside of upper face 38 of face member 12. Elastomeric member 16 includes a diaphragm 17 having a central plunger engaging diaphragm portion 44 and sensor engaging diaphragm portions 45, 46 at opposite ends of portion 44. An outer peripheral ridge 47a of member 16 and a second peripheral ridge 47c, which is inset from ridge 47a and somewhat lower in height define a groove 47b therebetween. The elastomeric member 16 is symmetric with respect to its upper and lower surfaces to define similar peripheral ridges 47a and 47c with a similar peripheral groove 47b therebetween, on the underside of the elastomeric member. Ridge 47a, groove 47b and ridge 47c encompass diaphragm portions 44, 45 and 46. An end tab 48 is integrally molded into the elastomeric member 16 at a distal end thereof to ensure correct placement of the member in the cassette 10 during assembly. Flapper valves 49a and 9b are integrally molded into the underside of elastomeric member 16 as best seen in FIGS. 3, 4c and 10. Note proximal sensing diaphragm portion 46 is smaller than distal sensing diaphragm portion 47 because flapper valve 49a is disposed outside distal sensing diaphragm portion 46 and within the central plunger engaging diaphragm portion 44 and flapper valve 49b is disposed within distal sensing diaphragm portion 47, to make the sensing areas of diaphragm portions 46, 47 approximately equal.

Base member 14 includes a generally box-like section 53 of rectangular configuration having a bottom wall 50, side walls 51a, 51b and end walls 52a, 52b. The juncture of side walls 51a, 51b and end walls 52a, 52b define a box section 53 and are rounded to conform the shape of the box section to the exterior shape of face member 12. Box section 53 of base member 14 is about 4.5 cm long and 2.0 cm wide. The side walls 51a, 51b and the end walls 52a, 52b are of uniform height (0.9 cm). The bottom wall 50 carries a base elliptic member 54 similar in shape to the face elliptic member 43 on face member 12, and generally conforming to the shape of the elastomeric member 16. The base elliptic member 54 includes an outer peripheral ridge 54a and a second peripheral ridge 54c somewhat lower in height and inset therefrom, to define a channel 54b therebetween. The structure of base elliptic member 54 conforms generally the structure of face elliptic member 43.

The interior of base elliptic member 54 includes a large central fluid chamber 22. Two smaller pressure monitoring chambers; i.e., a proximal pressure monitoring chamber 56 and a distal pressure monitoring chamber 57, are connected to opposite ends of central fluid chamber 22 and disposed along the longitudinal axis of the cassette 10.

Connected between proximal end wall 52a and proximal pressure monitoring chamber 56 is a tubular proximal fluid inlet channel 59 molded into the bottom wall 50 of base member 14. A similar distal fluid discharge channel 60 is connected between distal pressure monitoring chamber 57 and distal end wall 52b. A fluid inlet port 61 is molded into proximal end wall 52a of the base member 14 and connected to fluid inlet channel 59. A fluid discharge port 62 is molded into distal end wall 52b and connected to fluid discharge channel 60. Stiffeners or stiffening walls 63 extend from each of the end walls 52a, 52b to respective fluid inlet and fluid discharge ports 61 and 62 to provide a triangular support structure at each end of the base member 14 which retains and supports the fluid ports 61 and 62 mounted on the base member 14. Note also that the center fluid chamber 22 and the proximal and distal pressure monitoring chambers 56, 57 do not extend below the bottom of the side walls 51a, 51b of the base member 14.

Distal of the base elliptic member 54, between distal pressure monitoring chamber 57 and end wall 52b are provided cradle supports 64 mounted on the bottom wall 50 on the opposite sides of the distal fluid discharge channel 60. Cradle supports 64 are generally aligned with the cradle guides 42 of face member 12 when the base member 14 and the face member 12 are assembled. Switch stop 65 is mounted on the fluid discharge channel 60 distal of the cradle supports 64. Disposed in the side walls of the base member 14 are notches 71.

The assembled cassette is shown in FIGS. 5 and 6 in which the base member 14 receives the elastomeric member 16 which is then overlaid by the face member 12. Finally the flow stop 24 is inserted into the opening 35 in the face member 12 with the shaft 26 lowered along the cradle guides 42 to mount the flow stop 24 on opposite cradle supports 64 provided on the bottom wall 50 of base member 14.

The assembly of the cassette 10 is described in detail below and can be better understood if FIGS. 5 and 6 are considered in conjunction with the assembled cassette 10 of FIG. 1.

In FIGS. 5 and 6, the base member 14 receives the elastomeric member 16 on base elliptic member 54 as follows. Base elliptic member 54 of base member 14 receives elastomeric member 16, with outer peripheral ridge 54a of elliptic member 54 engaging the lower groove 47b of elastomeric member 16, and the outer ridge 47a of the elastomeric member disposed outside the outer ridge 54a of base elliptic member 54. Inner peripheral ridge 54c of member 54 traps inner lower ridge 47c of elastomeric member 16 within groove 54b of member 54.

With the elastomeric member 16 in place on the base member 14, Face member 12 is pressed down into the open box section 53 of the base member 14 to press outer peripheral ridge 43a of member 43 of face member 12 into upper groove 47b of elastomeric member 16. Inner peripheral ridge 43c of member 43 traps the upper inner ridge 47c of elastomeric member 16 within groove 43b of member 43. The specific configuration of face elliptic member 43, elastomeric member 16, and base elliptic member 154 and their interlocked assembly enable the member 16 to be solidly and fixedly retained in the cassette 10 in fluid-tight relation.

With elastomeric member 16 solidly disposed between the base member 14 and the face member 12 in fluid-tight engagement therewith, the members 12 and 14 are secured together by conventional means, e.g., sonic welding. When the cassette 10 is assembled check valves or "flapper" valves 49a and 49b are disposed closely adjacent respective opposite upper edges 20a and 20b of the recess 20 of base member 14.

In the cassette assembly of FIG. 1, plunger opening 18 of the face member 12 is aligned with the recess 20 of the base member 14.

The flow stop 24 is installed in the cassette 10 as follows. Switch body 25 is installed in the opening 35 of the face member 12 with shaft 26 sliding along cradle guides 42 of the face member 12 until the shaft 26 is disposed in the cradle supports 64 provided on the bottom wall 50 of the base member 14. Note in FIG. 3 that each of the cradle guides 42 includes an inwardly directed detent 42a at a respective lower end thereof so that in the installed position of the flow stop 24, shaft 26 slides past the detents 42a of the cradle guides 42 to be trapped between the lower ends of cradle guides 42 and the respective opposite cradle supports 64 of the base member 14.

In FIG. 5 the flow stop 24 is rotated clockwise to dispose the concave switch actuator 27 below the convex switch actuator 28 in an open position of the flow stop for cassette 10 with check valves or flapper valves 49a and 49b slightly open. The cassette 10 is in a free flow condition; i.e., the force of gravity on flapper valves 49a, 49b provided by fluid flowing into the cassette is sufficient to open the flapper valves and enable fluid flow through the cassette. Note that lower leg stop 29a of lower leg 29 of the flow stop 24 is disposed below detent 35b provided at a lower inner edge of distal end wall 34b of the face member 12 to hold the flow stop 24 in the open position of FIG. 5. Further, switch stop 65 engages the concave switch actuator 27 to prevent further rotation of flow stop 24 about shaft 26.

When the flow stop 24 is rotated about the shaft 26 to the engaged position of FIG. 6, stop 29a moves above the detent 35b to hold the flow stop in the position shown in FIG. 6 in which the lower end 30b of crown 30 engages the diaphragm of elastomeric member 16 to move flapper valve 49b into engagement with edge 20b of recess 20 to close the fluid path between inlet port 61 and discharge port 62. In the open position of FIG. 5 the cassette 10 could be primed outside the pump by allowing fluid to flow through the cassette, or the cassette could be primed in the pump as described below.

FIG. 7 shows a pump 69 including a pump housing 70 carrying therein a pump driver 72 including a plunger 73, a proximal pressure sensor 74 and a distal pressure sensor 75. The cassette 10, when installed in the pump housing 70, is held in place as by snaps 71a which engage the notches 71 in the side walls of the base member 14 to retain the cassette in the pump 69. The cassette 10 thus is mounted on the pump 69, with no door closing over the cassette or activating the cassettes. Because there is no pump door to protect the cassette 10, it is desirable to place all active cassette elements, such as plunger opening 18 and flow stop 24 at the pump/cassette interface. When the cassette 10 is installed in the pump 69 an engagement surface 76 on the pump engages the convex switch activator 28 to rotate the flow stop 24 to the closed position to prevent fluid flow through the cassette. The flow stop 24 thus operates as an auxiliary flow control member in conjunction with flapper valves 49a, 49b when the cassette 10 is loaded into the pump 69.

FIGS. 8 and 9 show the operation of the pump driver 72 when the cassette 10 is installed in the pump housing 70. The plunger 73 is engaged with and compresses the central portion 44 of the diaphragm of elastomeric member 16 during both the fluid inlet and the fluid discharge portions of the pumping cycle. The fluid inlet portion of the pumping cycle is shown in FIG. 8, wherein the plunger 73 is at the upper end of its stroke and the distal pressure sensor 75 engages upper end 30a of crown member 30 of the flow stop 24 to sense the pressure of fluid flowing through the fluid path of the cassette from the inlet port 61 to the discharge port 62. There is about seventy thousandths (0.070) inches of travel between the stop 29a and the detent 35b to enable the distal pressure sensor 75 to sense the pressure within the distal pressure monitoring chamber 57. When the plunger 73 reaches the peak of its pumping stroke as shown in FIG. 8, fluid inlet to the pumping chamber 22 is complete.

Thereafter the plunger 73 descends as shown in FIG. 9, and, under pressure generated by the descending plunger to compress fluid in the chamber 22, closes flapper valve 49a and opens flapper valve 49b against the bias of convex switch actuator 28 to enable fluid discharge from the pumping chamber 22 through the discharge channel 60 and then through discharge port 62. The movement of crown 30 against the distal pressure sensor 75 enables the flow stop 24 to sense distal pressure on the fluid discharge side of the cassette 10 throughout the working cycle of the pump, from the fluid inlet portion of the cycle shown in FIG. 8 through the fluid discharge portion shown in FIG. 9.

The intent of the present invention is to provide a simple, easily made disposable fluid pump cassette adaptable to a driver mechanism such as used in more sophisticated cassettes. The flow stop 24 provides the cassette 10 simple means for both controlling fluid flow and for measuring fluid pressure.

The present cassette does not require the extensive valving associated with the inlet and outlet of the cassette as required in prior art cassettes and the in-cassette air detection function for the present cassette is placed externally of the cassette, as for example on respective inlet and outlet lines of the cassette. Thus the present cassette offers a simpler, smaller, less expensive, and less complicated alternative to the complex and larger cassettes of the prior art.

A preferred embodiment of the present invention has been disclosed and described, other embodiments will become apparent to those of ordinary skill in the art. Such embodiments are not to be construed within the ambit of the claims which follow, unless by their terms, the claims expressly state otherwise.

We claim:

1. A flow stop mountable on a cassette, said cassette including a rigid base member and an upper member spaced from said base member to define a fluid flow path therebetween, said upper member including a flexible diaphragm mounted in said upper member in fluid tight relation thereto and adjacent said fluid flow path, said base member having upwardly extending protrusions therein to partially define a pumping chamber of the cassette, said diaphragm of said upper member having downwardly extending protrusions generally aligned with the upwardly extending protrusions of the base member to further define said pumping chamber, said base member protrusions and said upper member protrusions slightly displaced from each other to enable the flow path through the cassette, said flow stop including a switch body and a central shaft extending across the switch body to protrude on opposite sides thereof, said shaft mountable on the base member of the cassette to enable a rocking movement, a crown member disposed on the switch body to be placed adjacent the pumping chamber when the flow stop is mounted on the cassette, said switch body rockable about the shaft on an axis of the cassette between an open position enabling fluid flow through the cassette and an engaged position wherein the crown member is pushed downwardly to displace the diaphragm and drive at least one protrusion of said diaphragm into at least one protrusion of said base member to block the flow path and fluid flow through the cassette.

2. The flow stop as claimed in claim 1 wherein said shaft is mountable on cradle supports provided on the base member of the cassette.

3. The flow stop as claimed in claim 2 wherein the switch body includes two engageable portions which comprise a convex switch actuator disposed on one side of the shaft and a concave switch actuator disposed on an opposite side of the shaft for rockable movement about the shaft between said first and second positions.

4. The flow stop as claimed in claim 3 wherein the concave switch actuator includes an outer leg having a detent member provided at a lower end of the outer leg for engagement with a complementary detent on a distal end wall of the face member of the cassette.

5. The flow stop as claimed in claim 4 wherein the crown member is disposed at an extremity of the convex switch actuator, with a lower end of said crown member engageable with a pressure monitoring portion of the elastomeric diaphragm of the cassette, and an upper end of said crown member is adapted to be engageable with a pressure sensor associated with a pump driver.

* * * * *